US009509400B2

(12) United States Patent
Jain et al.

(10) Patent No.: US 9,509,400 B2
(45) Date of Patent: Nov. 29, 2016

(54) CIRCUIT ARCHITECTURE AND SYSTEM FOR IMPLANTABLE MULTI-FUNCTION AND MULTI-ANALYTE BIOSENSING DEVICE

(71) Applicants: Faquir C Jain, Storrs, CT (US); Fotios Papadimitrakopoulos, West Hartford, CT (US); Robert A Croce, Jr., Guilford, CT (US); Pawan Gogna, Clinton, MA (US); Syed Kamrul Islam, Knoxville, TN (US); Liang Zuo, San Jose, CA (US); Kai Zhu, Knoxville, TN (US)

(72) Inventors: Faquir C Jain, Storrs, CT (US); Fotios Papadimitrakopoulos, West Hartford, CT (US); Robert A Croce, Jr., Guilford, CT (US); Pawan Gogna, Clinton, MA (US); Syed Kamrul Islam, Knoxville, TN (US); Liang Zuo, San Jose, CA (US); Kai Zhu, Knoxville, TN (US)

(*) Notice: Subject to any disclaimer, the term of this patent is extended or adjusted under 35 U.S.C. 154(b) by 0 days.

(21) Appl. No.: 15/149,908

(22) Filed: May 9, 2016

(65) Prior Publication Data
US 2016/0254863 A1    Sep. 1, 2016

Related U.S. Application Data

(63) Continuation of application No. 14/023,116, filed on Sep. 10, 2013, now Pat. No. 9,337,924.

(51) Int. Cl.
*H04J 14/02* (2006.01)
*H04B 10/11* (2013.01)
*G01N 27/414* (2006.01)
*A61B 5/00* (2006.01)
*A61B 5/145* (2006.01)

(52) U.S. Cl.
CPC ............. *H04B 10/11* (2013.01); *A61B 5/0031* (2013.01); *A61B 5/14503* (2013.01); *G01N 27/4145* (2013.01)

(58) Field of Classification Search
CPC . H04J 14/02; H04B 10/1123; H04B 10/1143
See application file for complete search history.

(56) References Cited

U.S. PATENT DOCUMENTS

| 2008/0001735 A1* | 1/2008 | Tran | G06F 19/3418 340/539.22 |
| 2008/0004904 A1* | 1/2008 | Tran | A61B 5/0006 705/2 |
| 2008/0154101 A1* | 6/2008 | Jain | A61B 5/0017 600/309 |
| 2008/0223925 A1* | 9/2008 | Saito | G06Q 20/341 235/380 |
| 2009/0055735 A1* | 2/2009 | Zaleski | G06F 19/3406 715/700 |

* cited by examiner

*Primary Examiner* — Dzung Tran
(74) *Attorney, Agent, or Firm* — Steven M. McHugh

(57) ABSTRACT

An implantable bio-sensing platform architecture that enables the wireless selection, calibration and reading of multiple sensors, as well as checking the power levels of the solar powering source energizing various electronic and optoelectronic devices and circuits embedded in the platform. It also permits checking the operation of the potentiostats interfacing with each amperometric analyte sensor. The platform is flexible to include FET based sensors for protein sensing as well as other applications including pH sensing. In addition, other physiological sensors can be integrated in the platform.

2 Claims, 19 Drawing Sheets

CIRCUIT ARCHITECTURE AND SYSTEM FOR IMPLANTABLE MULTI-FUNCTION AND MULTI-ANALYTE BIOSENSING DEVICE

CROSS REFERENCE TO RELATED APPLICATIONS

This application is a continuation application and claims the benefit of U.S. patent application Ser. No. 14/023,116 which claims the benefit of priority of U.S. Provisional Patent Application Ser. No. 61/699,041 filed Sep. 10, 2012 and which is related to U.S. patent application Ser. No. 11/862,866 (U.S. Patent Publication No. 2008/0154101), the contents of both of which are incorporated herein by reference in their entireties.

STATEMENT REGARDING FEDERALLY SPONSORED RESEARCH

The United States Government has certain rights in this invention pursuant to National Institutes of Health Grant Nos. EB-011886 and HL-090458, National Science Foundation Grant No. IIP-1046902 and U.S. Army Medical Research and Materiel Command Grant Nos. W81XWH-09-1-0711 and W81XWH-07-1-0688.

FIELD OF THE INVENTION

This invention relates generally to bio-sensors and more particularly to implantable multi-function and multi-analyte biosensors.

BACKGROUND OF THE INVENTION

The continuous or on-demand measuring of one or two analytes using an implantable biosensor platform is described in the literature. As is known, amperometeric electrochemical sensing is one of the methods used in the detection of the analyte, including glucose and lactose. Field-effect transistor based and optical sensors are also employed.

Referring to FIG. 1, a multi-sensor circuit in accordance with the prior art is shown, where, although it has the ability to select one of many working electrodes or sensors, the multi-sensor circuit does not include a check potentiostat, check solar cell power methodology, and sensor calibration protocols. Accordingly, the multi-sensor circuit of the prior art is not able to check power, does not have potentiostat verification ability and does not provide an efficient design methodology which uses finite state machine and DSP based architectures. Additionally, reference is also made to published European Patent EP 1 680 676 B1 which describes a transcutaneous multi-analyte sensing system. However, this system is not fully implantable and does not have the means to wirelessly select a desired sensor, or wirelessly verify the powering and sensor calibration functions. Additionally, in the European design, the subject must be connected to an electronic interface at all times to obtain sensor readings with wires exiting the skin.

SUMMARY OF THE INVENTION

Disclosed herein is an implantable bio-sensing platform architecture that enables calibration and reading of multiple sensors including glucose, lactate, oxygen, and $CO_2$. It also enables checking power levels of the electrical source powering various electronic, optoelectronic and micro-electromechanical (MEM) components and circuits included in the implantable unit by receiving instructions from an external unit (not implanted). In addition, the architecture permits checking the operation of the potentiostats interfacing with the analyte sensors, as well as transmitting sensor readings and other data wirelessly back to the external unit.

Disclosed herein is an implantable bio-sensing platform architecture that enables the wireless selection, calibration and reading of multiple sensors, as well as checking the power levels of the electrical powering source energizing various devices and circuits embedded in the platform. It also permits checking the operation of the potentiostats interfacing with each amperometric analyte sensor. In one embodiment, mode selection (such as sensor calibration, sensor reading, power level check, potentiostat check) is carried out by finite state machine-based architecture. Operations such as receiving instructions from an external unit, performing desired tasks, and transmitting output data are carried out using optical communication link(s). In this embodiment, the powering of the implantable unit is carried out by utilizing optical sources located in the external unit which are incident on solar cells in the implantable unit. In other embodiments each sensor communicates its output data at a distinct optical wavelength which is received by the photodetector located in the external unit or proximity communicator. In yet another embodiment, each sensor is selected by activating a particular sensor using pulse coding architecture.

It is an object of the presently disclosed invention to provide advantages over currently available technologies that use electromagnetic radiation, such as in RF tags, for powering and communication. Those technologies result in devices that are generally too large for insertion and implantation through the use of a syringe or needle.

Further objects of the improvements disclosed herein are to provide: a finite state machine architecture for sending instructions to facilitate and control multiple functions; low power CMOS (complementary metal oxide semiconductor) circuits; smaller or miniaturized size for needle/syringe implantation; capacity for checking solar cell power levels; and capacity for potentiostat checking. As used herein the term "PDA" refers generally to devices known as personal digital/data assistants, and PDAs may be considered to be interchangeable with so-called "smartphones", "smart watches" and similar mobile devices that provide means for wireless communication and display.

BRIEF DESCRIPTION OF THE DRAWINGS

The foregoing and other features and advantages of the present invention will be more fully understood from the following detailed description of illustrative embodiments, taken in conjunction with the accompanying figures in which like elements are numbered alike.

BRIEF DESCRIPTION OF THE INVENTION

In accordance with an embodiment of the present invention, an implantable biosensor device having a bio-sensing platform architecture that enables calibration and reading of multiple sensors including glucose, lactate, oxygen, and $CO_2$ is disclosed herein. The implantable biosensor device also enables checking power levels of the electrical source that is powering various electronic, optoelectronic and micro-electromechanical (MEM) components and circuits that may be included in the implantable unit. This may be accomplished via any method suitable to the desired end purpose, such as for example by receiving instructions from an external unit (not implanted). In addition, the architecture may permit checking the operation of the potentiostat(s) that interface with the analyte sensors, as well as transmitting sensor readings and other data wirelessly back to the external unit.

Figure 1:
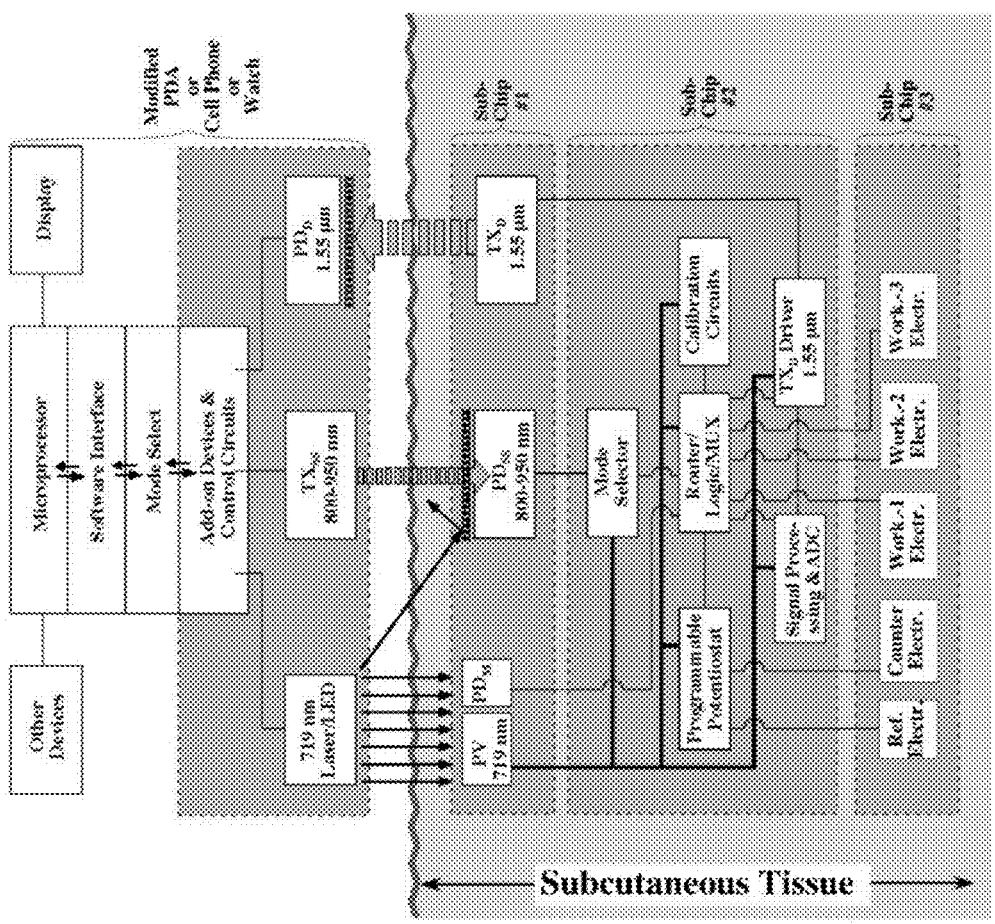
FIG. 1 is a schematic diagram illustrating a multi-sensor circuit, in accordance with the prior art.

Referring to FIG. 1, a sensor circuit in accordance with the prior is shown where the sensor circuit does not have a check potentiostat and check solar cell power methodology, etc. However, it has ability to select one of many working electrochemical sensors.

Figure 2A:
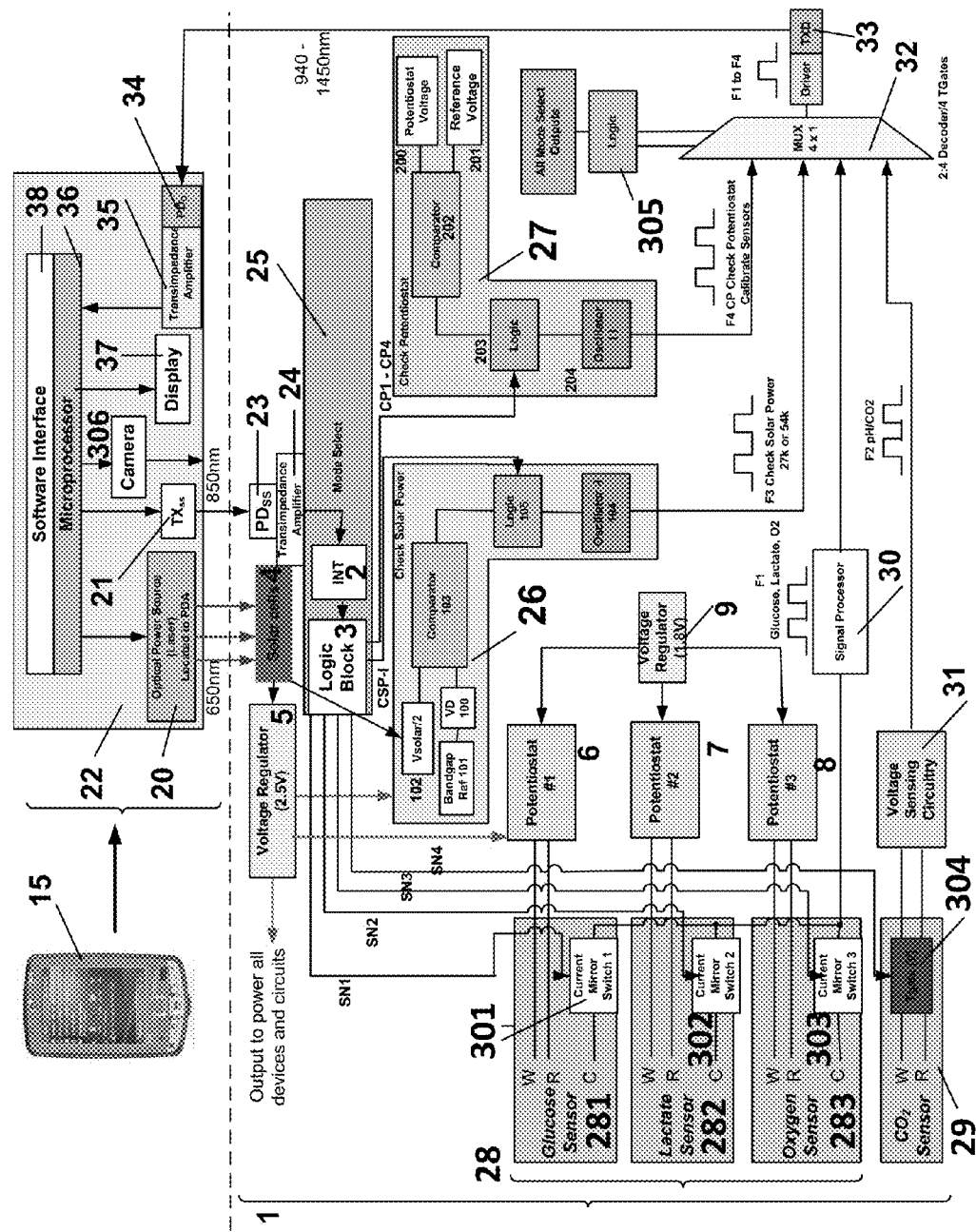
FIG. 2A is a schematic diagram illustrating the architecture of an implantable multi-analyte sensor device, in accordance with one embodiment of the invention.

Referring to FIG. 2A, the overall architecture for the multi-analyte monitoring system is shown, in accordance with an embodiment of the invention. The external unit 22 in this embodiment consists of a PDA or smart-phone accessory 15 which may be embedded with all the electronic/optoelectronic components required to communicate with the implanted multi-analyte sensor chip 1. Here, the external unit 22 contains two optoelectronic components: (1) a LED/laser 20 to provide electromagnetic radiation for powering the circuits and (2) a function selection transmitter $TX_{ss}$ 21 used to send encoded optical pulses. The function selection transmitter, $TX_{ss}$ 21, located in external unit 22 sends a particular number of pulses depending on the function desired. The optical pulses (e.g. generated by an 850 nm laser or LED transmitter 21) are received in the implanted device by a photodetector, $PD_{ss}$ 23. The output of the photodetector is then converted into voltage pulses via a transimpedance amplifier 24. These electrical pulses serve as the clock input to a Mode-Select block 25 which in turn selects an output using interface electronics 2 and logic block 3. It should be appreciated that in some embodiments, the optical pulses may be frequency and/or amplitude based. It should be further appreciated that these outputs (10 available outputs for a 16-pulse state machine, which includes RESET function) may be comprised of four (or more or less) sensors SN1-SN4, four (or more or less) check potentiostat circuits CP-1 to CP-4, check solar power circuit CSP-O and CSP-I.

The laser/LED power source 20 powers the solar cells 4 whose output is stabilized by a voltage regulator 5, which in turn supplies power to all devices and circuits. For example, in one embodiment, power is fed to three potentiostats labeled as 6, 7, and 8. These potentiostats are shown with a dedicated voltage regulator 9, if needed. This architecture may also contain check solar power CSP-I pins connected to check solar power block 26 and one of the four check potentiostat outputs CP-1 to CP-4 connected to the check potentiostat block 27. These circuits ensure the operation as desired. It should be appreciated that in other embodiments other configurations may be used to accomplish this function. The logic block outputs SN1-SN4, when activated by the coded pulses, activate on the switches 301, 302, 303 to enable one of three shown amperometric sensors 28 (shown individually as 281, 282 and 283). The voltammetric sensor 29 is enabled by switch 304. The amperometric switches 301, 302, 303 are configured to pass current, while the voltammetric switch 304 is configured to pass voltage. The resulting signal from each amperometric sensor may be sent to the signal processing unit 30 and the signal from the voltammetric sensor 304 may be fed to the voltage sensing circuitry 31. The signals from the signal processing unit 30, voltage sensing circuitry 31, as well as the check solar power 26 and the check potentiostat blocks 27 are sent to a multiplexer (MUX) 32 which feeds them to optical transmitter 33 (via its driver 330), when the MUX is enabled.

The MUX 32 enables one of its multiple inputs using logic circuits 305, which in turn are enabled by the output of Logic Block 3 in the Mode Select unit 25. The optical transmitted $TX_D$ 33 output is received by the external unit 22 where it is converted into electrical pulses by the photodetector, $PD_D$ 34. A transimpedance amplifier 35 in the external unit 22 amplifies the photodetector 34 pulses which are communicated to the microprocessor 36 to be decoded and sent to the display 37. The microprocessor also communicates with the software interface 38 which allows the user to input desired functionalities. Additionally, the microprocessor controls the camera 306 which enables alignment of the implanted chip 1 with the external unit 22, which may be housed in a portable (or non-portable, if desired) device 15, such as a smart phone or PDA. In one embodiment, the display 37 could be the display of smart phone 15. Similarly, the microprocessor 36 and software protocol may be replaced by the embedded processor of the smart phone 15. Details of check solar power 26 and check potentiostat 27 are provided in FIG. 6 and FIG. 7, respectively. Referring to FIG. 4 and FIG. 5, details of one embodiment of the circuit used to realize the mode select unit 25 is shown. In another embodiment, the electrochemical sensor may be a three electrode sensor with a Working electrode (W), a Reference electrode (R), and a Counter electrode (C). In other embodiments, it is contemplated that some sensors may have just two electrodes as shown for $CO_2$ sensing. Accordingly, it should be appreciated that the number of electrode sensors may, in part, be based on desired functionality.

Figure 2B:
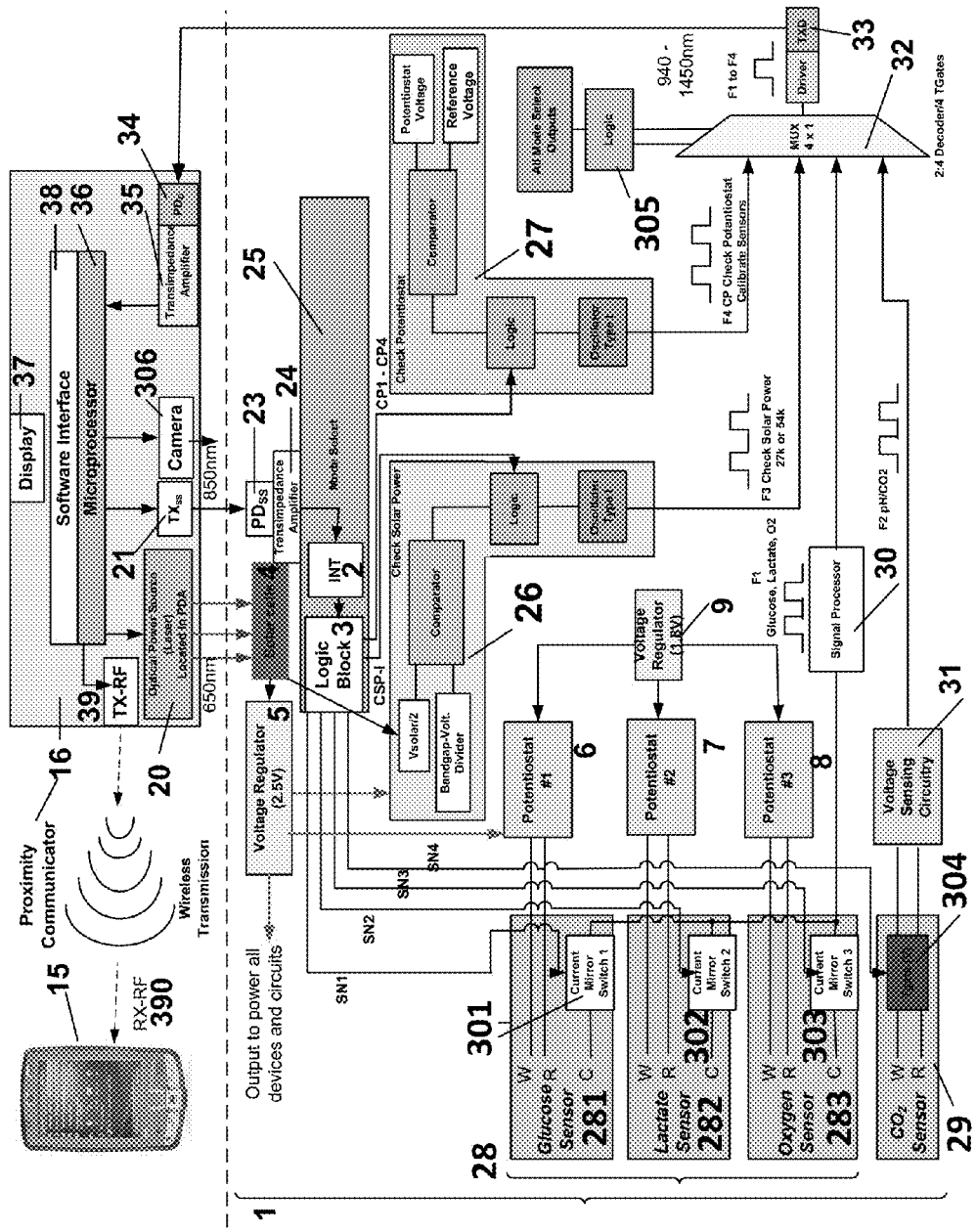
FIG. 2B is a schematic diagram illustrating a proximity communicator interfacing with the multi-analyte sensor device of FIG. 2A and a portable device.

Referring to FIG. 2B the architecture as shown is similar to the architecture of FIG. 2A. However, in this embodiment a stand-alone external unit, called the proximity communicator 16 is provided and includes some or all of the electrical/optoelectronic powering, microprocessor, and communication devices 21 ($TX_{ss}$) and 34 ($PD_D$) used to communicate with the implanted chip platform 1 wirelessly. Moreover, it may also transmit (using TX-RF 39) the received information to a device 15, such as a PDA, smartphone or laptop accessory. The proximity communicator 16 in one embodiment is envisioned as a "smart watch" like device. Depending on the application, many proximity communicators can communicate via smart phone to a cloud based server which can be accessed by health care providers.

Figure 3A:
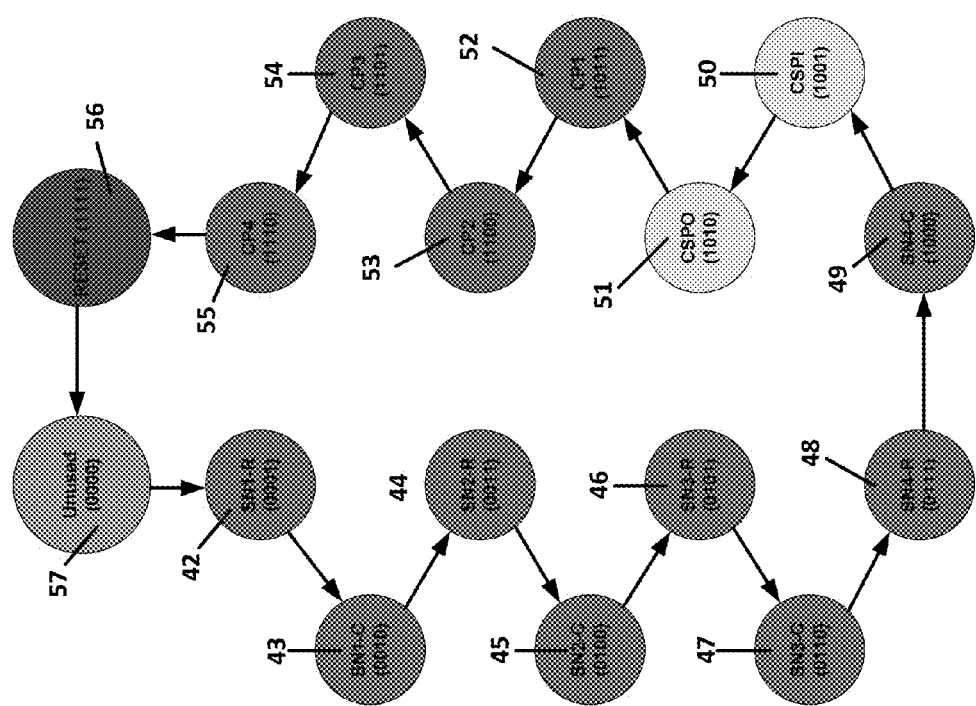
FIG. 3A is a flow diagram illustrating the finite state machine output being used for mode selection, in accordance with one embodiment of the invention.
Figure 3B:
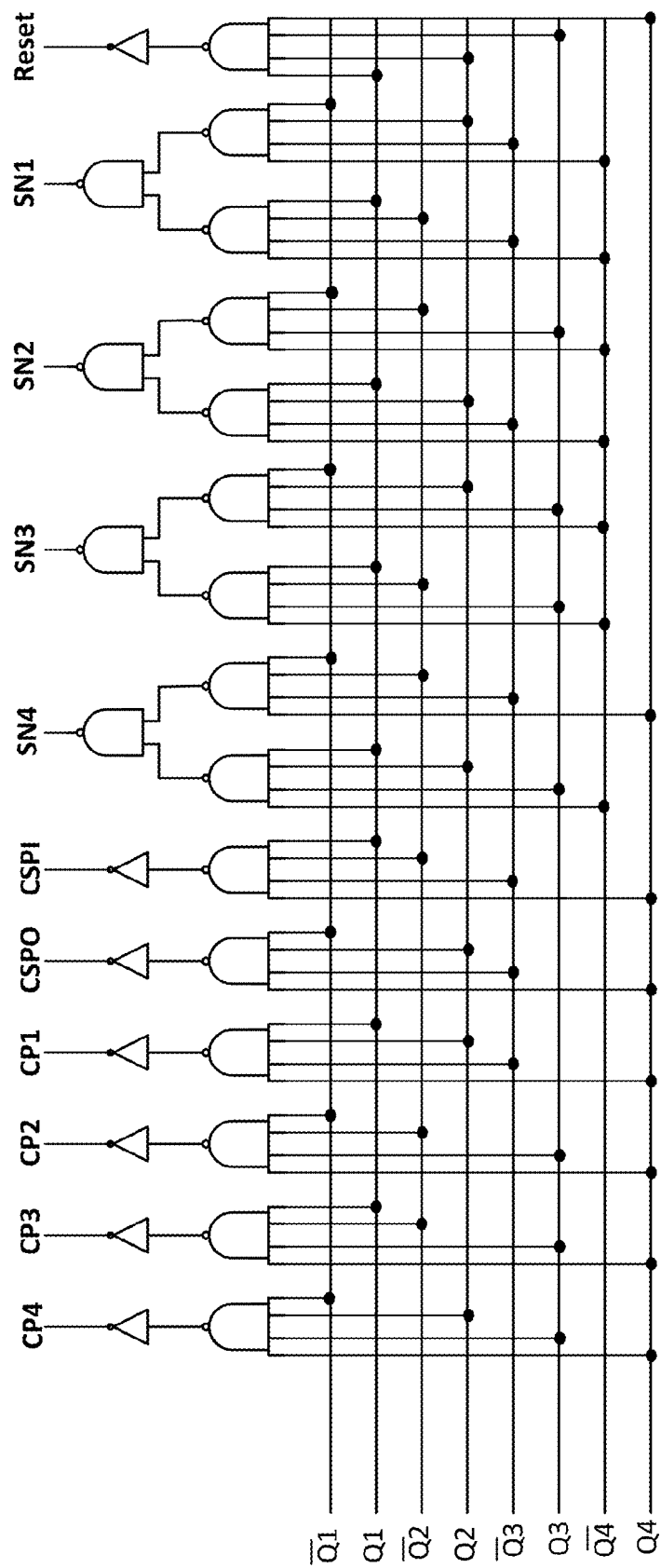
FIG. 3B is a schematic diagram illustrating the logic block for the finite state machine of FIG. 3A, in accordance with one embodiment of the invention.

FIG. 3A illustrates a flow chart of how the outputs move through the state machine, and FIG. 3B illustrates the schematic of the state machine logic. Referring to FIG. 3A and FIG. 3B, the optical pulses received by $PD_{ss}$ 23 serve as the input to a 4-bit counter 40 which is used as the input to the state machine logic circuit 41 and successively changes the output state. Here, the SN1-R 42 corresponds to reading the value of the sensor #1 and SN1-C 43 corresponds to the calibration of sensor #1. SN2-R 44 corresponds to reading the value of sensor #2 and SN2-C 45 corresponds to the calibration of sensor #2. Similarly, SN3-R 46 means reading the value of the sensor #3 and SN3-C 47 means calibrating sensor #3. SN4-R 48 corresponds to reading the value of sensor #4 and SN4-C 49 corresponds to the calibration of sensor #4. The check solar power circuit (CSPI) 50 output checks the solar cell power before any voltage regulation and CSPO 51 checks the output following the regulator. CP1 52 initiates checking the voltage level of potentiostat #1, CP2 53 initiates checking the voltage level of potentiostat 2, CP3 54 initiates checking of the voltage of potentiostat #3 and CP4 55 initiates checking the voltage level of potentiostat #4. FIG. 3B illustrates the schematic of logic block 3 components in one embodiment. Here, sensor select SN1-SN4, check potentiostat CP1 to CP4, check solar power output CSP-O and CSP-I are shown along with the Reset pin.

Figure 4A:
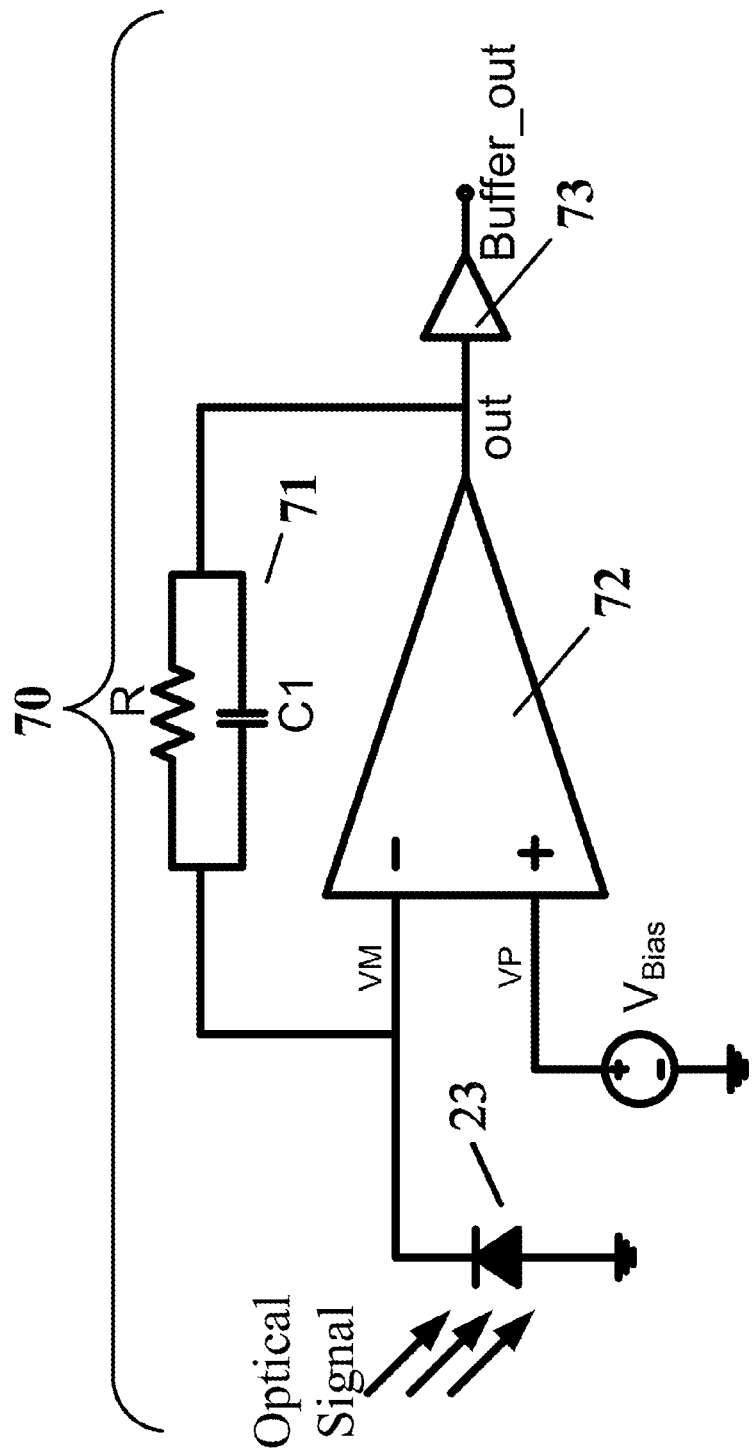
FIG. 4A is a schematic diagram illustrating the on-chip photodetector, $PD_{SS}$, and transimpedance amplifier used to amplify the coded signal received by the photodetector of the implantable multi-analyte sensor device of FIG. 2A, in accordance with one embodiment of the invention.
Figure 5:
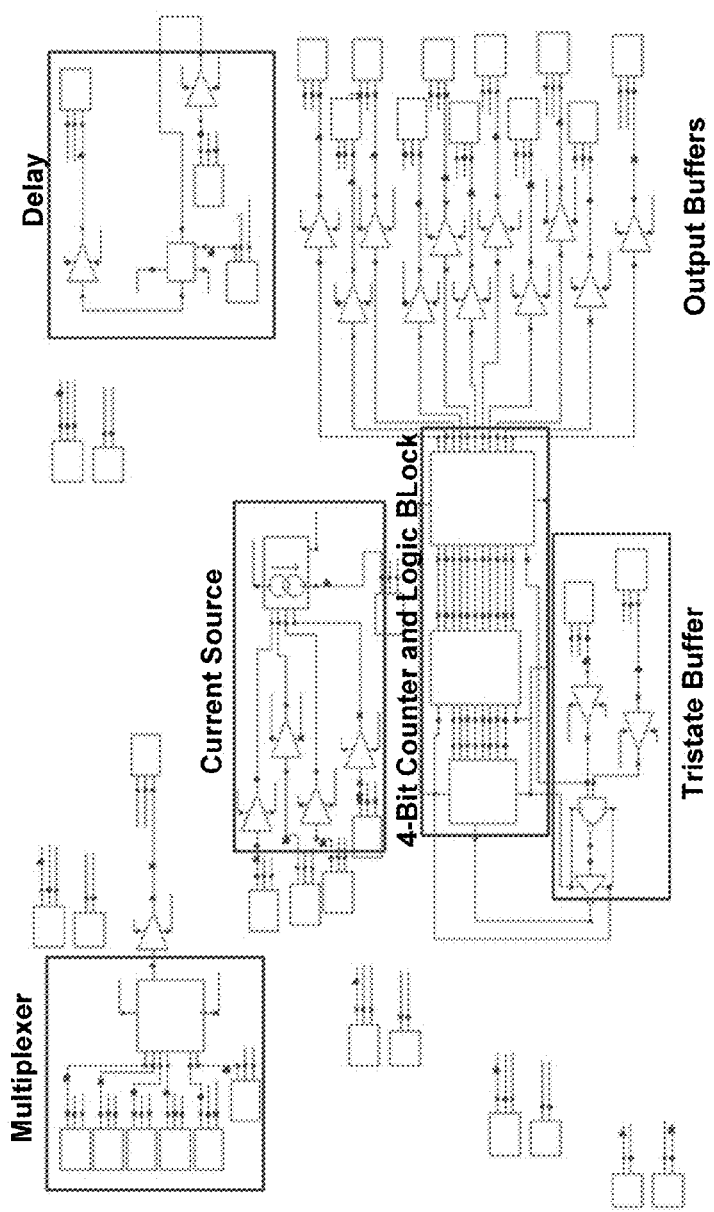
FIG. 5 is a schematic block diagram illustrating circuit blocks that form the mode select function of FIG. 4B, in accordance with one embodiment of the invention.

FIG. 4A shows an embodiment of how the optical pulses are transmitted from transmitter $TX_{ss}$ 21, located in an external unit 22 (See FIG. 2A), and are received by the photodetector $PD_{SS}$ 23 and converted into electrical voltage pulses to be used as the clock input of the Mode Select Block 25. This Mode Select Block consists of an on-chip silicon photodiode 23 whose signals get amplified by a transimpedance amplifier circuit 70 consisting of a feedback RC network 71 an operational amplifier 72 and an output buffer 73.

Figure 4B:
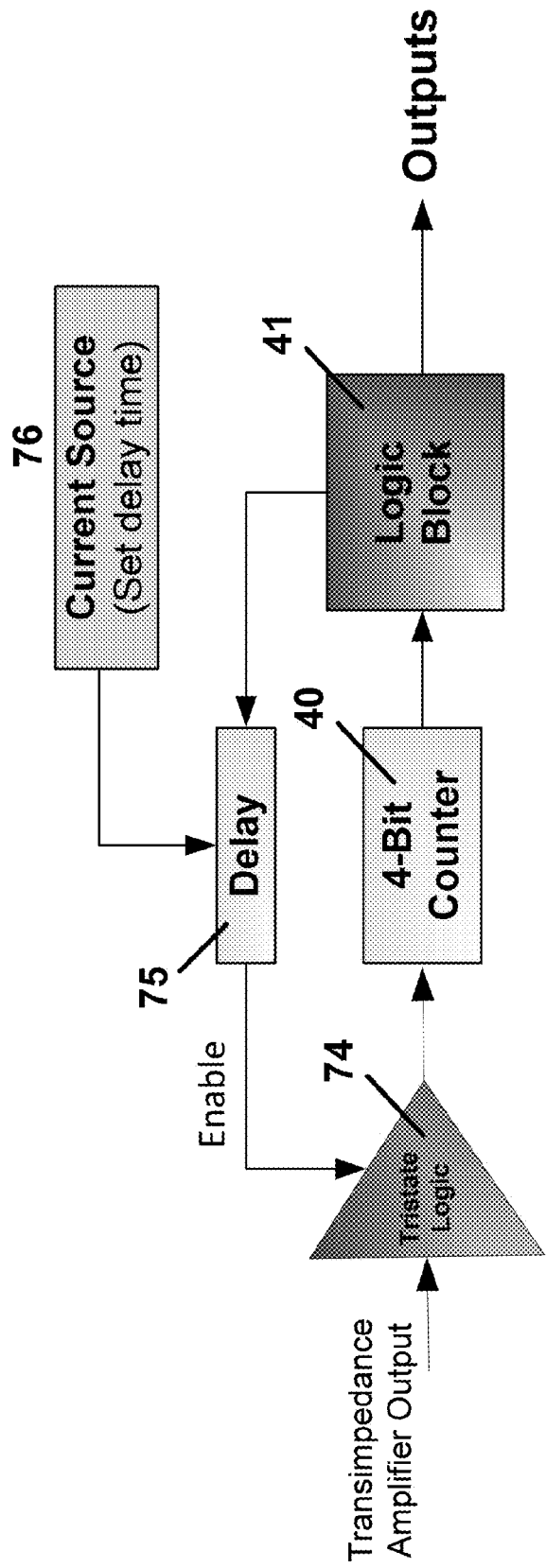
FIG. 4B is a schematic block diagram illustrating a Mode Select Circuit Block Diagram of the implantable multi-analyte sensor device of FIG. 2A, in accordance with one embodiment of the invention.

FIG. 4B illustrates using a block diagram the functionality of Mode Select Circuit. It consists of a tri-state logic (or buffer) 74 which, when enabled, sends the electrical pulse train from the transimpedance amplifier 70 to the 4-bit counter 40. The output of the 4-bit counter 40 is then used as the input to the logic block 41 which enables the selection of a desired output. A delay circuit 75 is used as the control functionality of the tri-state buffer 74 to allow the electrical pulses to be sent to the 4-bit counter only once the state-machine has reached its initial state 41. This delay circuit is activated once the 'Reset' output of the state machine has been reached 56, and the delay time is controlled by a current source 76.

FIG. 5 below shows detailed circuit schematic of various building blocks of FIG. 4B, in accordance with one embodiment. The output of Mode Select Circuit also goes to the selection bits of the multiplexer which enables connection of the appropriate output (sensor output, check solar power output, etc.) to the optical output transmitter, $TX_D$.

Figure 6A:
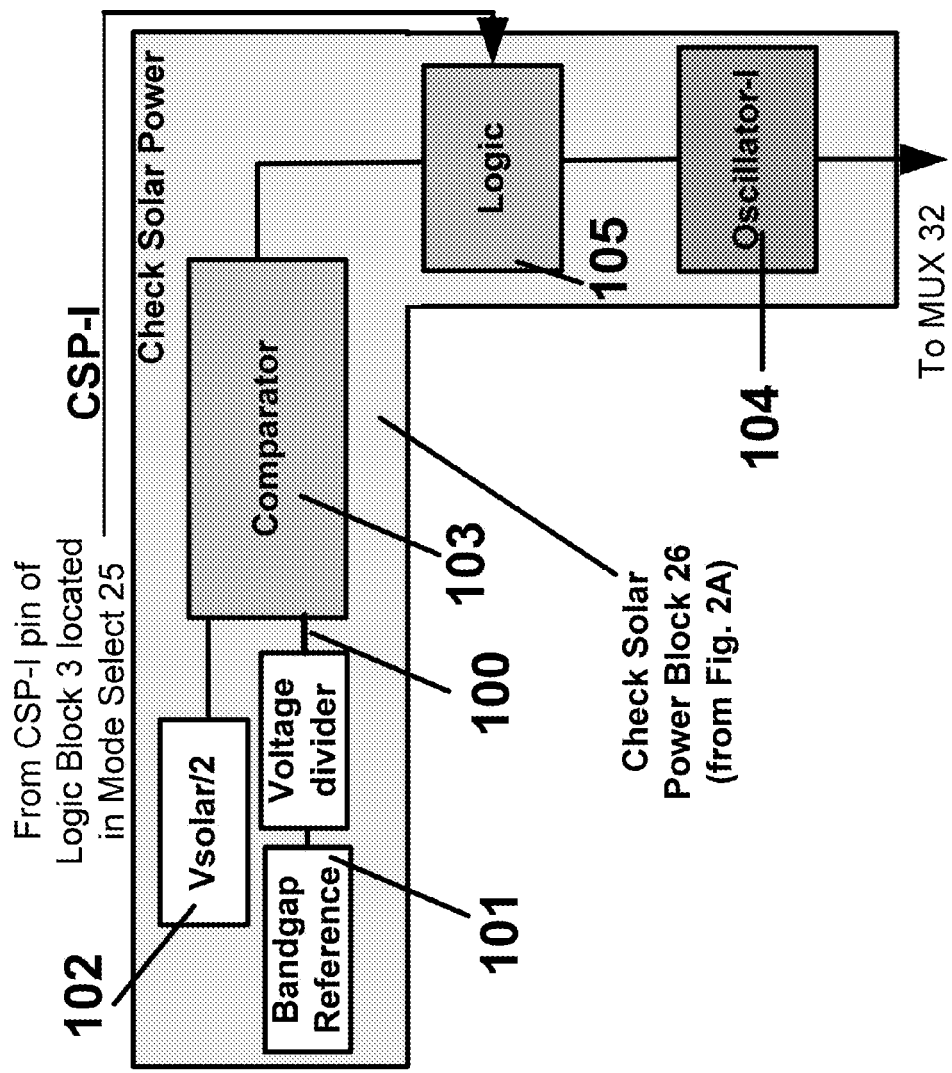
FIG. 6A is a schematic block diagram of the Check Solar Power Block of the implantable multi-analyte sensor device of FIG. 2A, in accordance with one embodiment of the invention.
Figure 6B:
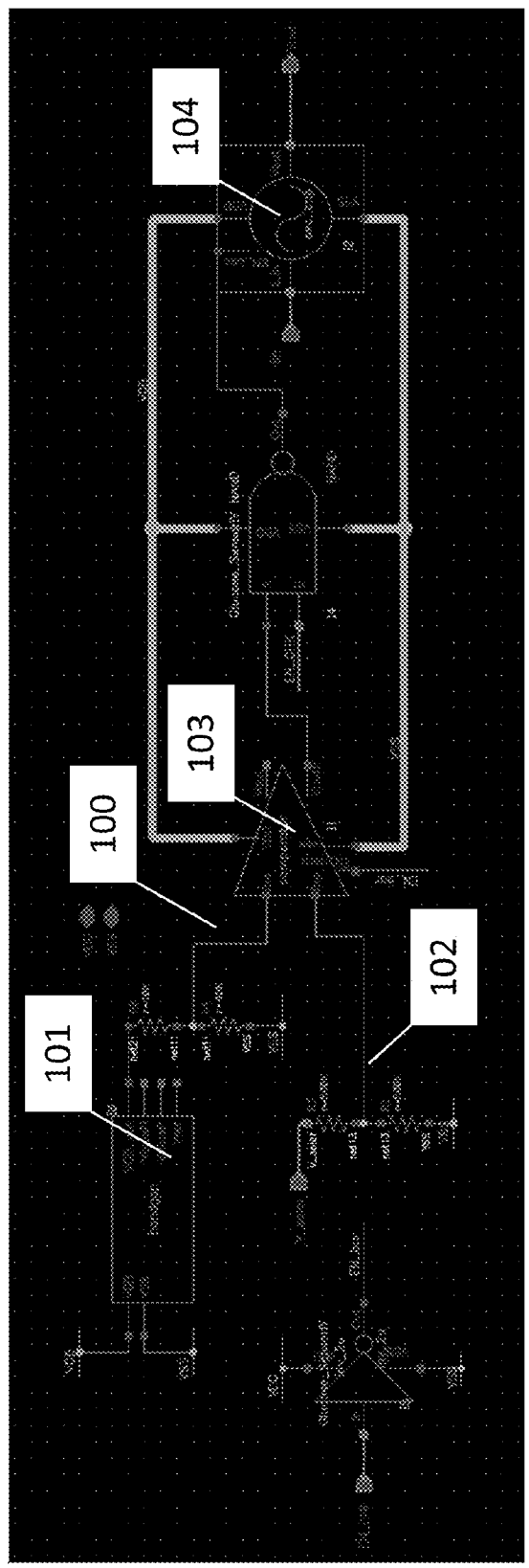
FIG. 6B is a circuit level schematic diagram of the check solar power circuit (CSPI) of FIG. 6A, which has a comparator and an oscillator which produces pulses at a set frequency, in accordance with one embodiment of the invention.
Figure 6C:
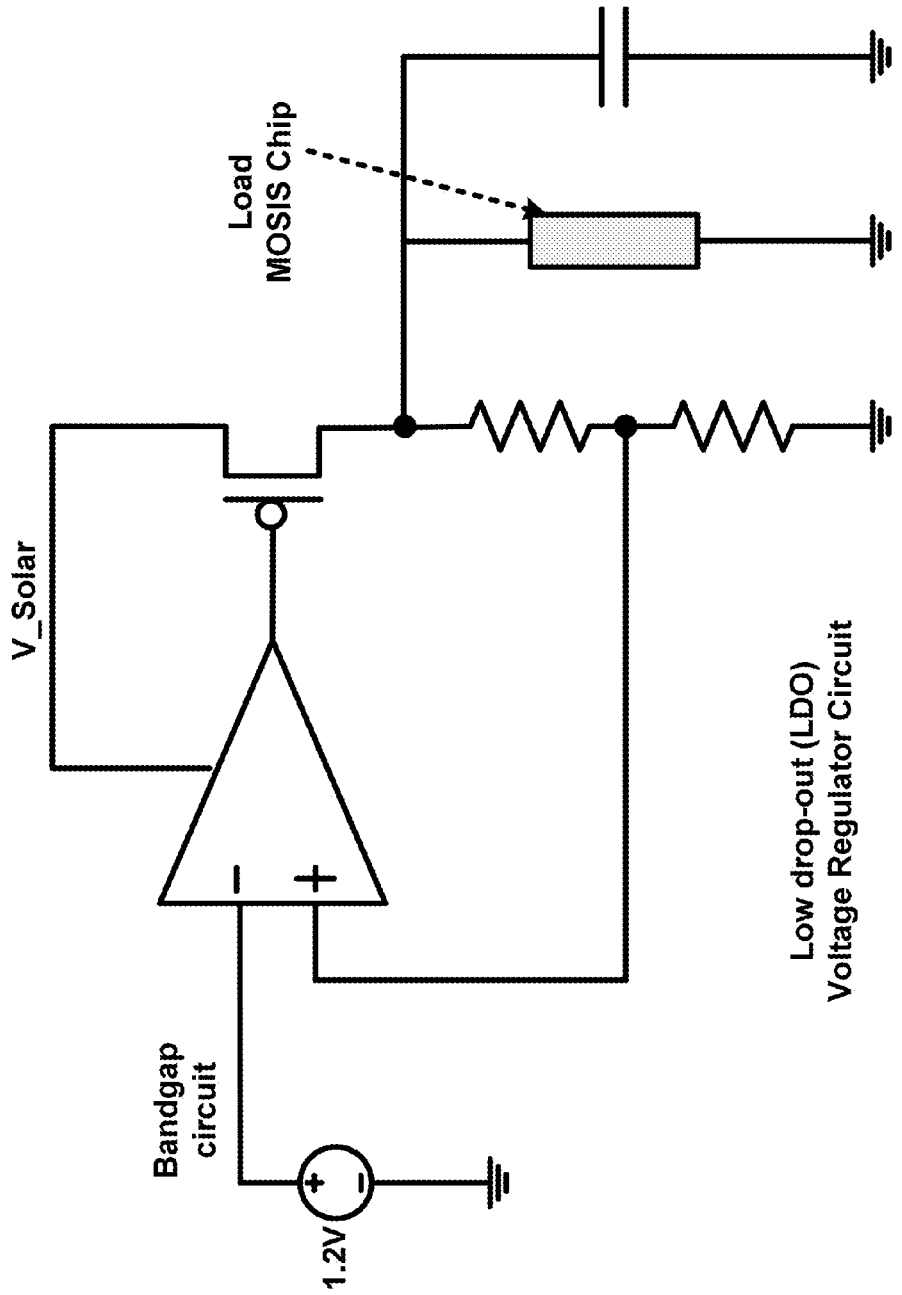
FIG. 6c is a schematic diagram illustrating a voltage regulator circuit used in the implantable multi-analyte sensor device of FIG. 2A, in accordance with one embodiment of the invention.

Referring to FIG. 6A, a schematic of the check solar power block (see FIG. 2A) is shown, in accordance with one embodiment. This circuit implements a reference voltage (via resistive divider) 100 from an on-chip band-gap circuit 101 and compares that with a voltage-divided solar cell output 102. Once the value of the voltage-divided solar cell output is above the reference voltage, by means of a comparator 103. The comparator output is enabled by a logic circuit which serves as a switch enabled by the CSP-I output pin from the Mode Select Logic block 3. Once the oscillator 104 is turned ON, its output is fed to the multiplexer 32 and is connected to the output transmitter $TX_D$ 33. Referring to FIG. 6B, a schematic of check solar cell power circuit 26 is shown in accordance with one embodiment. Referring to FIG. 6C, the schematic of the voltage regulator circuit which then receives the solar cell voltage and supplies a stable power for the system is shown in accordance with one embodiment.

Figure 7A:
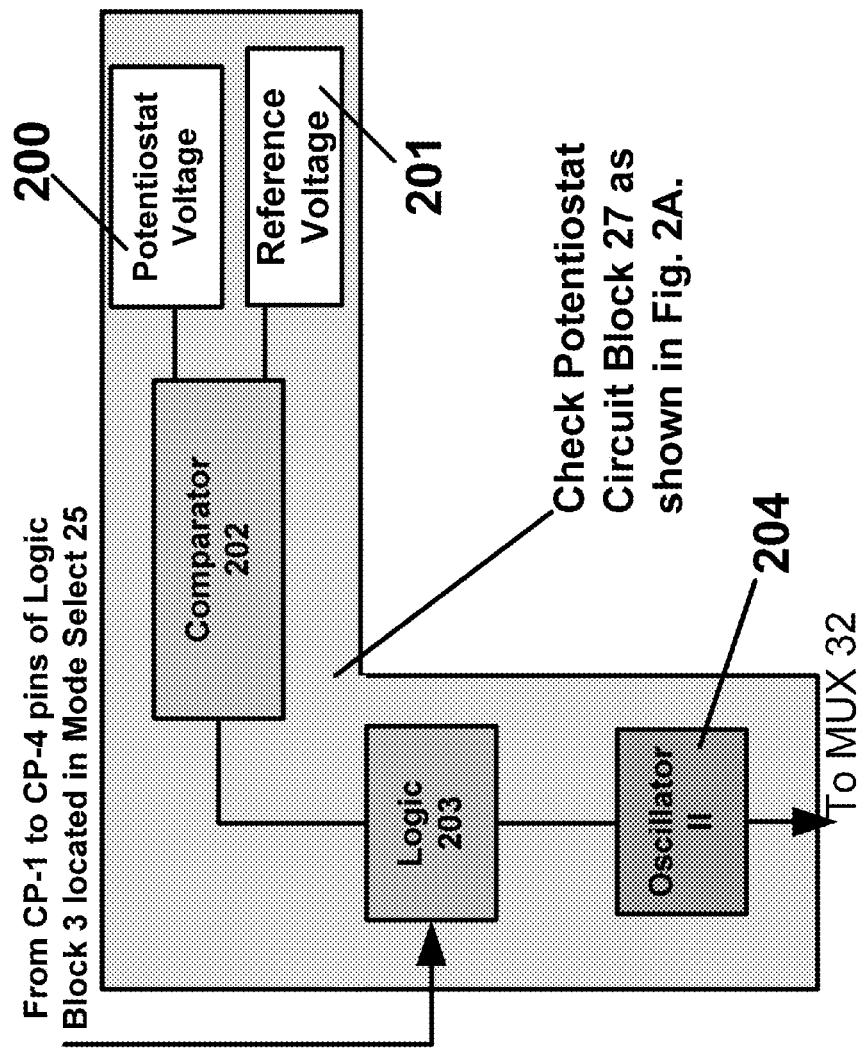
FIG. 7A is a schematic block diagram illustrating a check potentiostat circuit block used in the implantable multi-analyte sensor device of FIG. 2A, in accordance with one embodiment of the invention.
Figure 7B:
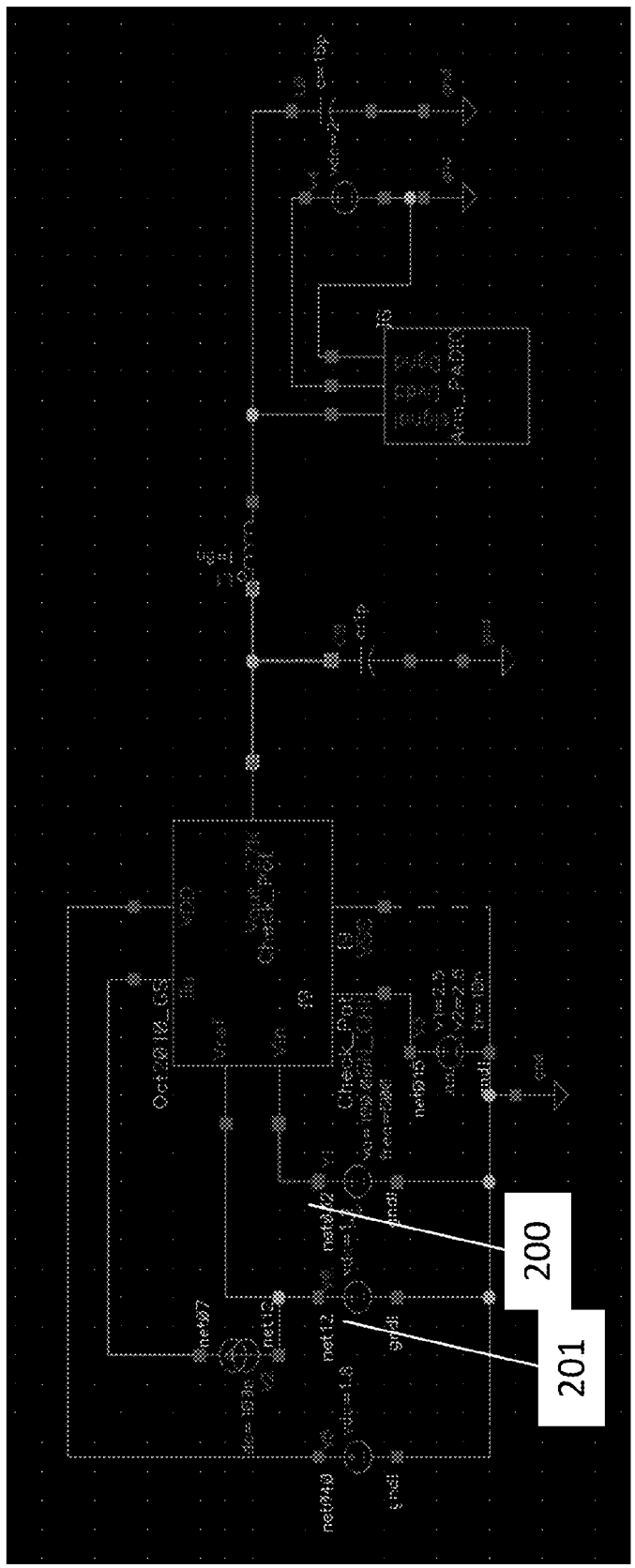
FIG. 7B is a circuit level schematic diagram illustrating the check potentiostat circuit block of FIG. 7A.

Referring to FIG. 7A, a check potentiostat circuit block is shown (see FIG. 2A), where the potentiostat working electrode-reference electrode voltage 200 is compared in a comparator 202 with a reference voltage 201. This voltage is obtained by a voltage-divided bandgap circuit similar to one shown in FIG. 6A where the comparator output is fed to a logic circuit 203 which acts as a switch which is turn ON when enabled by CP-1 to CP-4 signal received from the Logic Block 3 of Mode Select 25. The frequency of oscillation is different than that for the Check Solar Power Circuit. Referring to FIG. 7B, a circuit schematic of a check potentiostat circuit block, which operates in a similar manner as the Check Solar Power circuit shown in FIG. 6, is illustrated in accordance with one embodiment.

Figure 8:
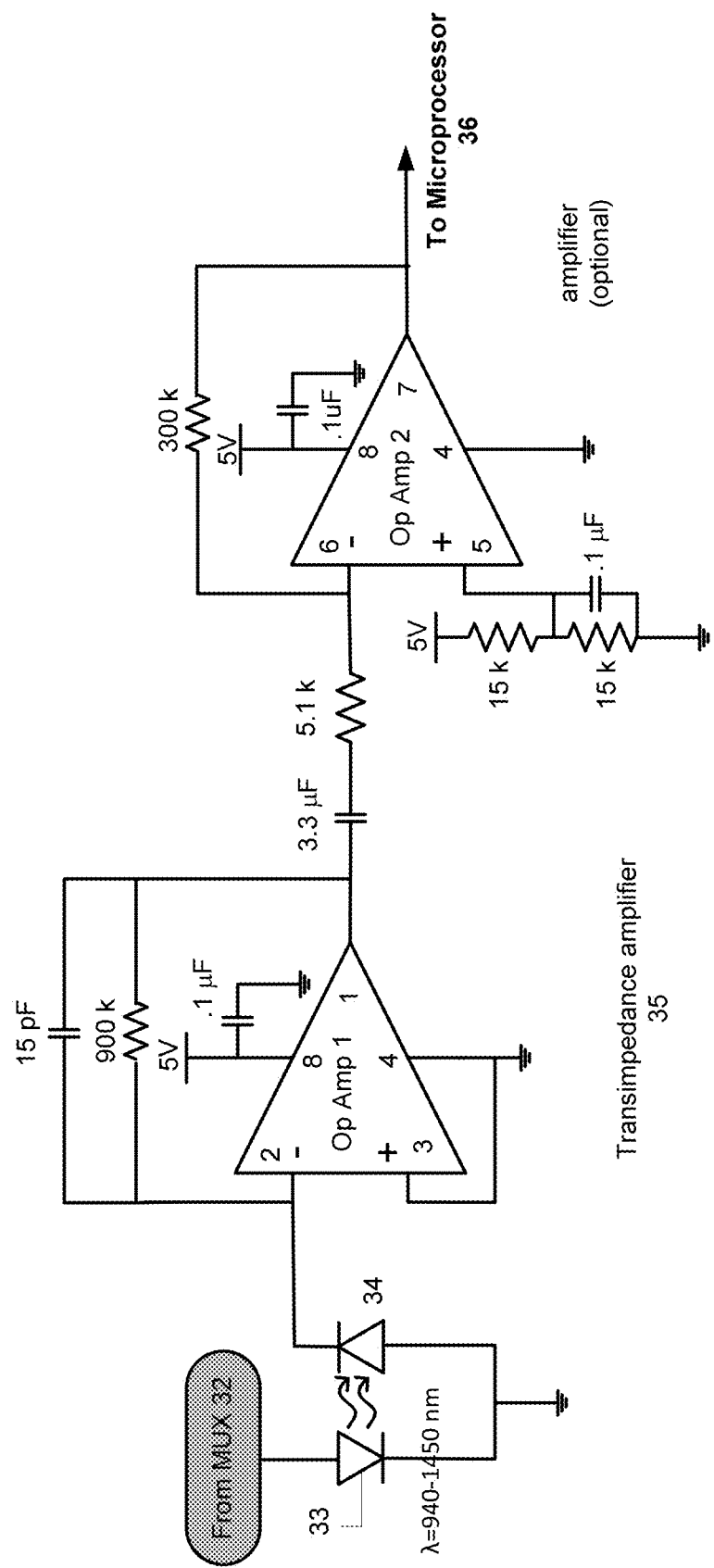
FIG. 8 is a schematic diagram of a photodetector $PD_D$ along with a transimpedance amplifier to receive optical signals from the implant and produce an electrical output used in the implantable multi-analyte sensor device of FIG. 2A, in accordance with one embodiment of the invention.

Referring to FIG. 8, a photodetector, $PD_D$ 34 along with a transimpedance amplifier used to receive sensor data from the transmitter, $TX_D$ 33 on the implantable device and produce electrical output pulses is shown in accordance with an embodiment of the invention. The optical pulses from $TX_D$ 33 are received by an photodetector $PD_D$ 34 located in the PDA 15 (see FIG. 2A). The transimpedance amplifier 35 which may be located in the external unit 15 converts the electrical current from receiver 34 into voltage pulses which can be counted by a microprocessor and displayed 37, or stored in the PDA memory.

Figure 9:
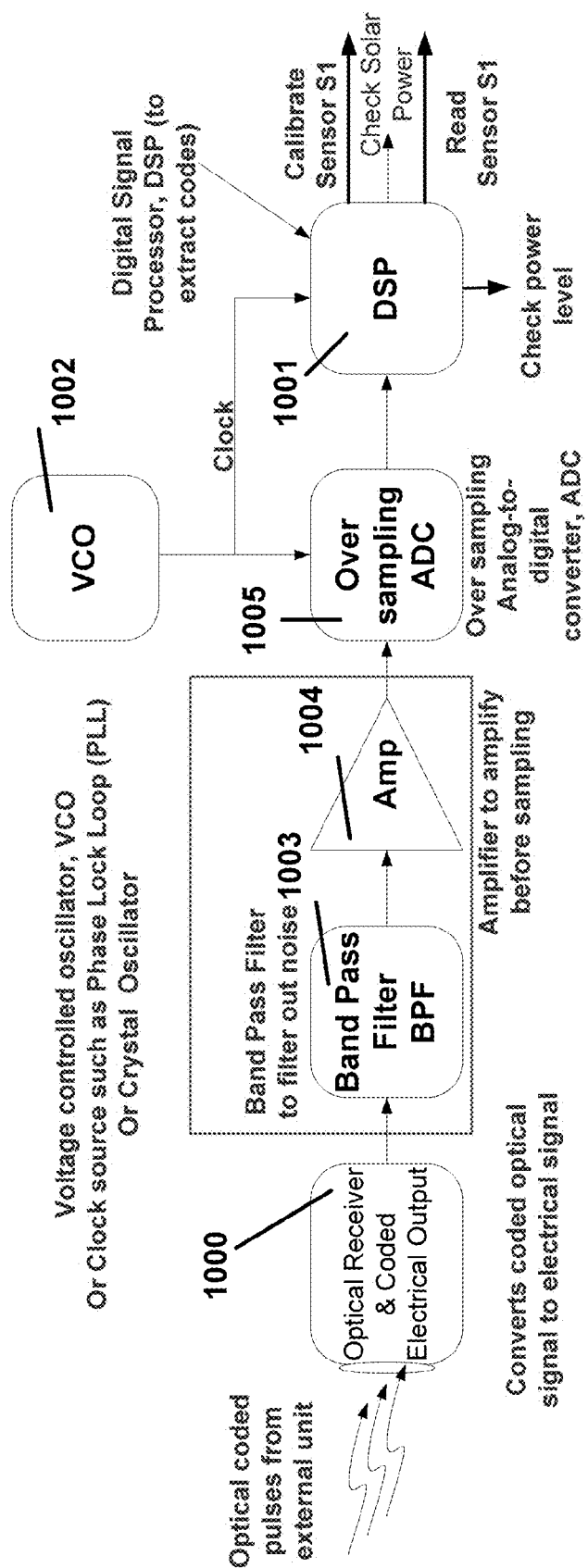
FIG. 9 is a block diagram illustrating a digital signal processor (DSP) based circuit architecture for multi-sensor selection used in the implantable multi-analyte sensor device of FIG. 2A, in accordance with one embodiment of the invention.

Referring to FIG. 9, a block diagram illustrating one embodiment of a DSP-based circuit architecture that is different from the finite state machine described above in FIG. 2 is shown. The coded optical signal from the external unit 22 (FIG. 2A) is received by the "optical receiver and digital electrical output" block 1000. The output of 1000 may be filtered by a band pass filter 1003 and amplified 1004. This output from 1004 is communicated to an over-sampling analog to digital converter ADC 1005, where the ADC 1005 may include a clock generated by voltage control oscillator VCO 1002. The output of ADC 1005 and generated clock may be fed to a Digital Signal Processing (DSP) 1001 unit where the code is deciphered with the help of an internally generated clock signal from a voltage controlled oscillator (VCO) 1002. The output of the DSP 1001 may activate (via a logic circuit) a particular sensor, check potentiostat, check solar power function block on the implantable platform. This sensor outputs, potentiostat check outputs, solar check outputs are signal processed like that shown in FIG. 2 circuit block and fed to a MUX 32 and to a optical transmitter 33. The output of transmitter 33 is received by the external control unit's 22 receiver $PD_D$ 34.

In another embodiment in relation to FIG. 9, the clock may be generated by a phase lock loop (PLL), voltage controlled oscillator and/or by a crystal oscillator. Here the incoming optical signal (which may include instructions) is converted to electrical signal(s) which in turn is digitized. The digitized signal is processed by the digital signal processing (DSP) block to extract the instruction. Then the instruction is processed and executed to carry out tasks such as calibration, measurement, save data to non-volatile memory, save instructions to non-volatile memory, transmit data from sensors or non-volatile memory etc. It is contemplated that even more functions as desired could be included with these instructions.

Figure 10:
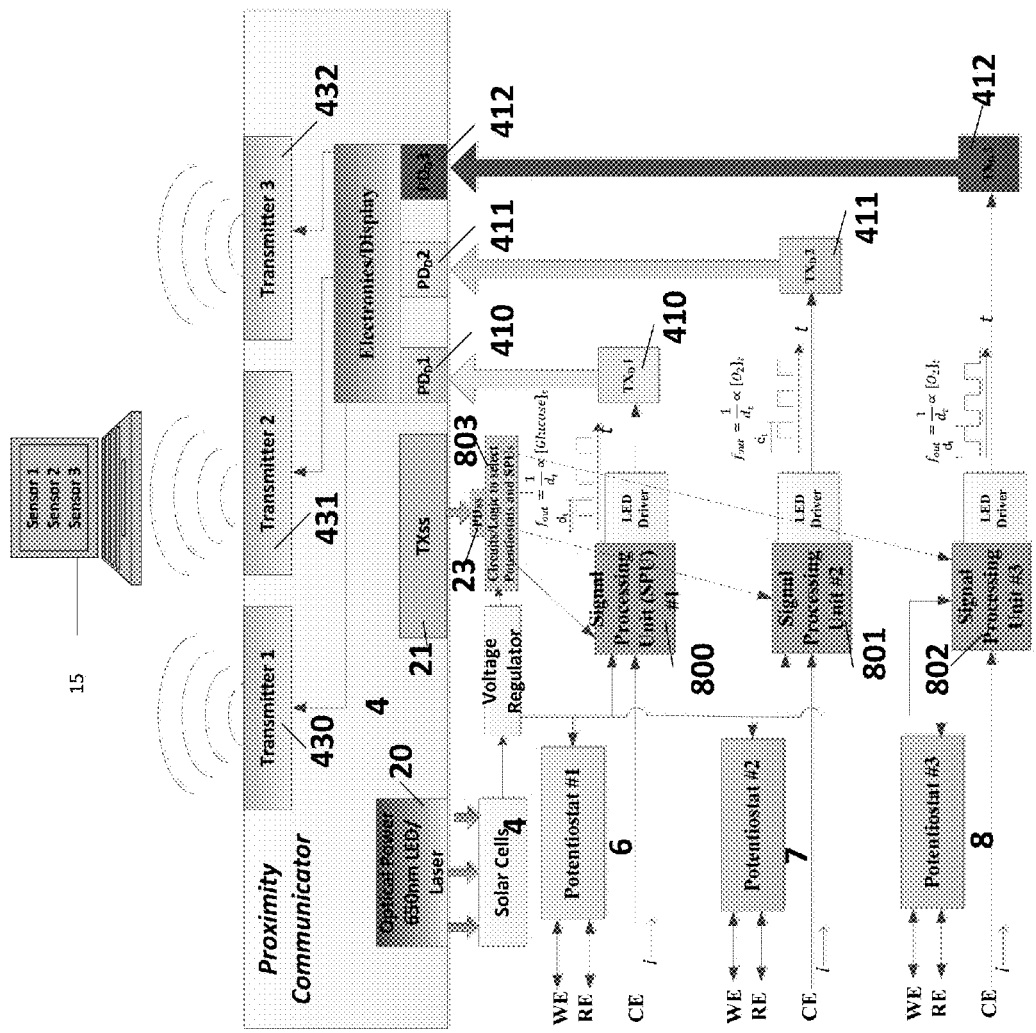
FIG. 10 is a block diagram illustrating multiple sensors communicating at multiple wavelengths, in accordance with one embodiment of the invention.

Referring to FIG. 10, a block diagram of a sensing methodology where dedicated optical transmitters and receivers are used for each type of sensors is illustrated in accordance with one embodiment of the invention. In this embodiment, signal processing unit #1 800, signal processing unit #2 801 signal processing unit #3 803 is selected by the logic selector 803 by receiving optical instructions. Optical instructions are sent/received similar to that of FIG. 2A/FIG. 2B which incorporates the transmitter TXss 21 and photodetector receiver PDss 23. The sensor readings are transmitted at distinct optical wavelengths ($TX_D1$ 410, $TX_D2$ 411, and $TX_D3$ 412) which is received by photodetectors (PD1 510, PD2 511, $P_D3$ 512) located in the external unit or proximity communicator. Data is then transmitted by 3 separate transmitters; Transmitter 1 430, Transmitter 2 431, and Transmitter 3 432 to a smart phone or PDA accessory 15. Also similar to that of FIG. 2A/FIG. 2B, the unit may be powered by an Optical Power Source (LED/Laser) 20 which may be incident on (or close enough to) the solar cells 4.

Figure 11:
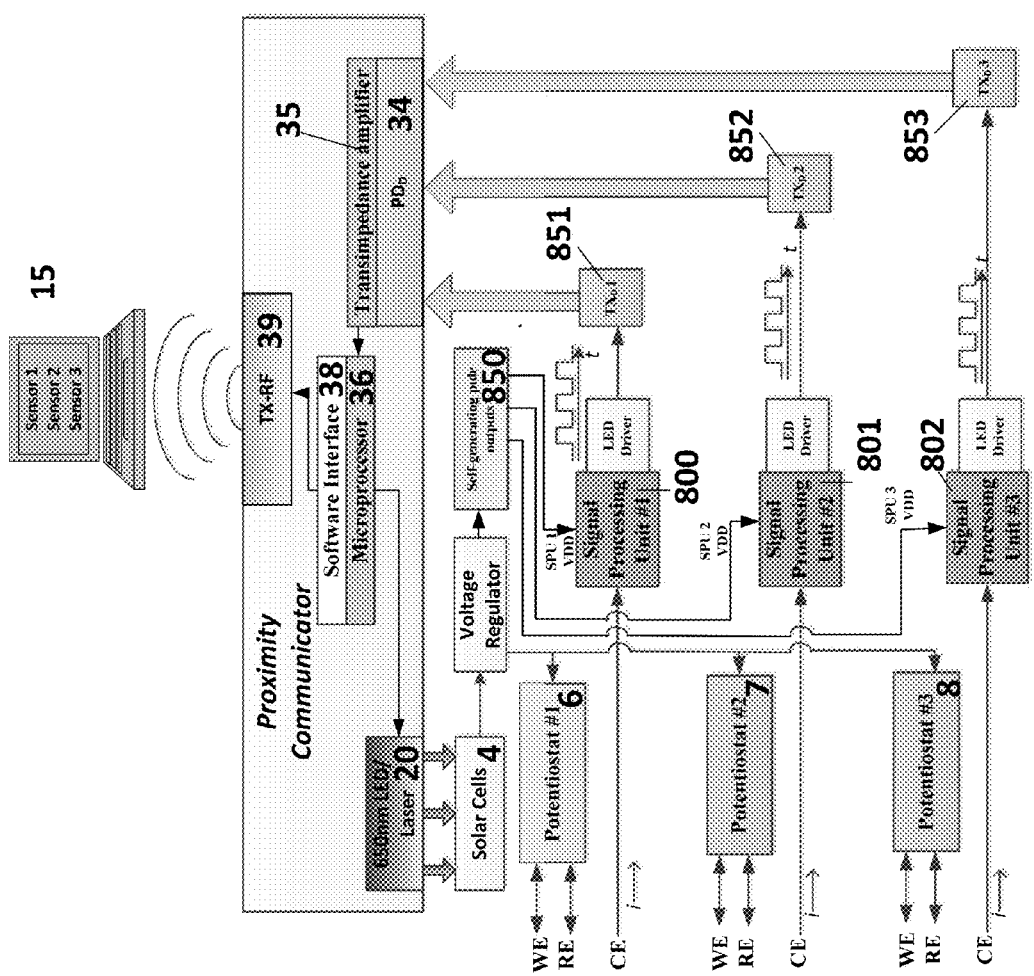
FIG. 11 is a schematic block diagram illustrating a biosensor architecture configured to allow the selection of multiple sensors using self-sequencing circuits, in accordance with one embodiment of the invention.

Referring to FIG. 11, a block diagram of multiple potentiostats interfacing with multiple signal processing units is illustrated in accordance with one embodiment of the invention. As show, each signal processing unit may be activated by a self-generating state machine output circuit 850 that supplies power to a signal processing unit #1 800, signal processing unit #2 801 and signal processing unit #3 802 at different times. The sensor output is then sent to transmitters TXD1 851, TXD2 852 and TXD3 853 (operating at the same wavelength) where it is received by $PD_D$ 34 proximity communicator. Sensor information is decoded on the proximity communicator by the microprocessor 36 and software interface 38 and linked to the respective sensors by the order in which it was received then transmitted by TX-RF 39 to a smart-phone or personal digital accessory electronic device 15. Like FIG. 2A/FIG. 2B, the unit may be powered by a Optical Power Source (LED/Laser) 20 which is incident on (or close enough to) the solar cells 4.

Figure 12:
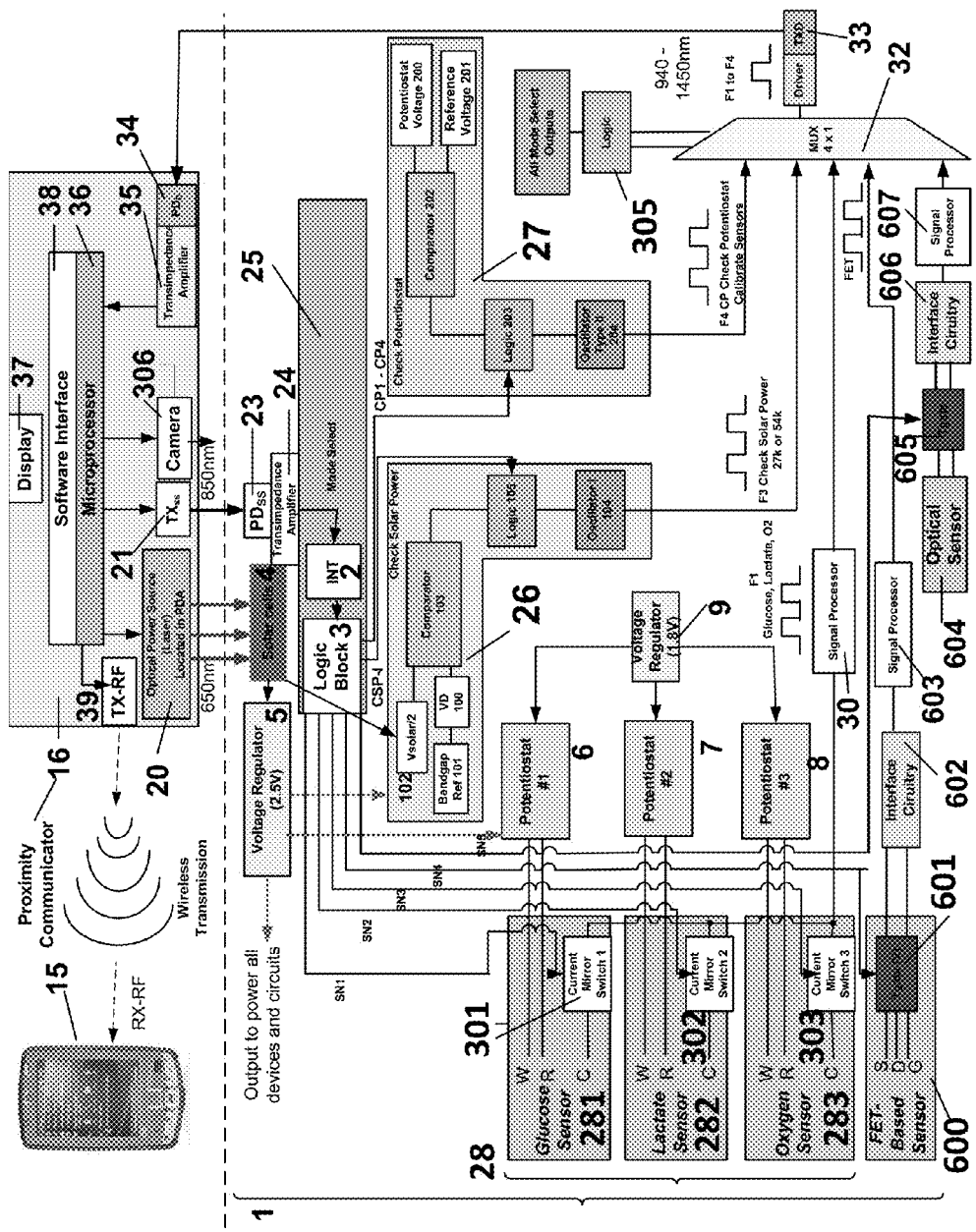
FIG. 12 is a schematic block diagram illustrating a biosensor architecture that integrates amperometeric/Voltammetric, FET-based, and optical sensors, in accordance with one embodiment of the invention.

Referring to FIG. 12, architecture similar to FIG. 2A/FIG. 2B which integrates amperometeric/voltammetric, FET-based sensor 600, and optical sensors 604 is illustrated in accordance with one embodiment of the invention.

Figure 13:
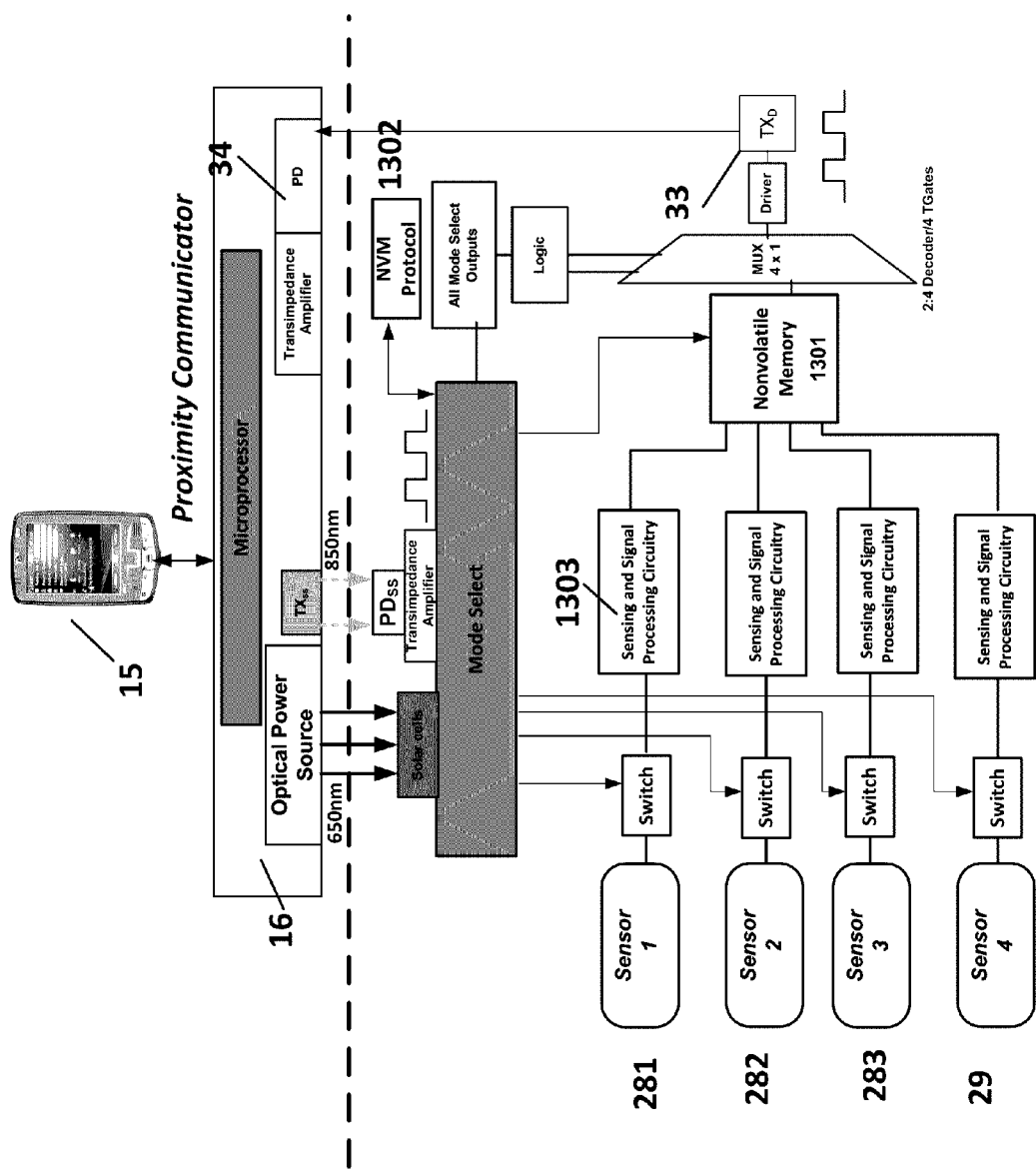
FIG. 13 is a schematic block diagram illustrating a system design that uses nonvolatile memory (NVM) for storing data and protocols, in accordance with one embodiment of the invention.

Referring to FIG. 13, another embodiment of a system design that employs nonvolatile memory (NVM) block 1301 for storing sensor readings and other calibration data, and when enabled the MUX transmits the stored data at predesigned intervals is shown. NVM block 1301 may store sensor self-calibration routines/protocols to correct any sensor malfunction or aging effects. In another embodiment, NVM 1301 may also store routines/protocols for calibration and measurement sequences as well as timing of such events. The timer in the design helps the chip make such calibrations and measurements at pre-decided times or time intervals. The results of such measurements could be transmitted back to the receiver or stored in a nonvolatile memory block like NVM 1301 with built-in analog-to-digital and digital-to-analog converters. The measurements at specified time intervals may be used to help track the time trend for the bio sensor measurements. Time trend measurements may also help establish correlation between the levels of various bio-sensing elements. In yet another embodiment, the optical receiver $PD_{ss}$ 23, transimpedance amplifier 24, depending on the coded pulses received from $TX_{ss}$ 21, enable NVM 1301 protocols to execute Mode Selection functionalities. In this embodiment, sensors 281-283, 29, switches and signal processing units 1303 may be variations of blocks shown in FIG. 2A/FIG. 2B.

In another embodiment, the optical coded pulses may be received by the implantable device and solar powering may be used. However, the output data may be transmitted using a frequency modulation (FM) scheme by replacing optical transmitter $TX_D$ with an oscillator and a frequency modulation circuit. The output of this modulated transmitter circuit may be fed to an antenna and broadcast the readings received from the multiplexer. The FM signal is now received by the dedicated FM receiver chip in the external control unit/proximity communicator.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

We claim:

1. An implantable bio-sensing platform chip that enables the wireless selection, calibration and reading of multiple sensors, wherein the bio-sensing platform receives optical power and coded optical instructions from an external control unit located in proximity of the implanted sensor platform chip, the bio-sensing platform comprising:
   sensors,
   sensor interface circuits,
   signal processors,
   electronic multiplexers,
   solar cells, and
   optoelectronic transmitters and receivers that wirelessly communicates with said external unit, wherein the platform receives from the optical transmitter located in the external control unit coded pulses using at least one photodetector operating at the dedicated wavelength and converting them to electrical pulses, wherein solar cells are interfaced with at least one voltage regulator circuit whose output provides stable power to the entire platform electronic circuits and optoelectronic transmitters and receivers, and a radio frequency (RF) transmitter wherein the carrier wave is modulated depending on the output of signal processing unit and transmitting RF waves using an antenna located on the biosensing platform,
   and where in the RF wages are received by the RF receiver located in the external unit,
   wherein coded electrical pulses are decoded using finite state machine architecture by the mode select unit interfacing with the said photodetector receiving the coded pulses,
   wherein mode select unit comprising of logic circuits enabling various functions depending on the code pulses,
   wherein coded pulse sequence in one code enables operation of checking solar power output providing information regarding the level of electrical power generated by the solar cells by sending a dedicated frequency voltage pulse train which drives a voltage controlled oscillator serving as a FM transmitter or a dedicated RF transmitter with a specific frequency range and located on the implanted platform,
   wherein the output of the FM transmitter is transmitted using an antenna located on the bio-sensing platform,
   wherein coded pulse sequence in one embodiment enables checking of operation of a potentiostat interfacing with a bio-sensing element before bio-sensing element code is sent for taking readings, wherein the output of said voltage controlled oscillator or a FM transmitter is received by a dedicated FM receiver located in the external control unit, and wherein FM receiver in the external control unit output is processed and displayed,
   wherein coded pulse sequence in another coded sequence enables calibration and reading of a designated biosensor, wherein the bio-sensing platform sensors include analytic sensors, protein biosensors, and physiological sensors, the analyte sensors being connected to interface electronics, signal processing unit, and multiplexer, and wherein the multiplexer output feeds a driver that in turn feeds the said FM transmitter which converts electrical pulses into FM pulses.

2. The bio-sensing platform of claim 1 wherein the mode select unit is interfaced with a first nonvolatile memory, and wherein the instructions and subroutines are stored,
   wherein the nonvolatile memory based routines are executed in a predetermined way as the coded pulse sequence or signals are received from the external control unit via its optical transmitter and received by the dedicated receiver or photodetector located in the implanted bio-sensing platform,
   wherein coded pulse sequence received from the external unit enables calibration and reading of a designated biosensor, and
   wherein in one embodiment the calibration and biosensor data is stored in second nonvolatile memory following signal processing unit, and wherein the processed calibration and sensor reading data is transmitted via the RF transmitter upon getting instructions using the multiplexer unit,
   and wherein the transmitted data is received by a dedicated RF receiver in the external control unit.

* * * * *